United States Patent [19]

Thompson

[11] Patent Number: 5,362,233
[45] Date of Patent: Nov. 8, 1994

[54] ORTHODONTIC APPLIANCE

[76] Inventor: William J. Thompson, 6610 Riverview Blvd., West, Bradenton, Fla. 34209

[21] Appl. No.: 20,754

[22] Filed: Feb. 22, 1993

[51] Int. Cl.⁵ .............................................. A61C 3/00
[52] U.S. Cl. .................................... 433/9; 433/10; 433/14
[58] Field of Search .................. 433/8, 9, 10, 13, 14, 433/16

[56] References Cited

U.S. PATENT DOCUMENTS

| | | |
|---|---|---|
| 1,821,171 | 9/1931 | Atkinson . |
| 2,125,587 | 2/1938 | Richardson . |
| 2,196,516 | 4/1940 | Atkinson . |
| 2,305,916 | 12/1942 | Atkinson . |
| 2,686,365 | 8/1954 | Schurter . |
| 2,716,283 | 8/1955 | Atkinson . |
| 2,908,974 | 10/1959 | Stifter . |
| 2,971,258 | 2/1961 | Bien . |
| 3,119,182 | 1/1964 | Miller et al. . |
| 3,128,553 | 4/1964 | Begg . |
| 3,163,933 | 1/1965 | Begg et al. . |
| 3,178,822 | 4/1965 | Fogel et al. . |
| 3,262,207 | 7/1966 | Kesling . |
| 3,335,496 | 8/1967 | Andrews et al. . |
| 3,423,833 | 1/1969 | Pearlman ............... 433/8 X |
| 3,435,527 | 4/1969 | Kesling ..................... 433/14 |
| 3,521,355 | 7/1970 | Pearlman ............... 433/8 X |
| 3,574,940 | 4/1971 | Allesee . |
| 4,212,638 | 7/1980 | Korn .......................... 433/8 |
| 4,227,876 | 10/1980 | Fogel et al. ............... 433/11 |
| 4,242,085 | 12/1980 | Wallshein ................. 433/14 |
| 4,310,306 | 1/1982 | Wallshein ................. 433/14 |
| 4,427,381 | 1/1984 | Hall .......................... 433/14 |
| 4,496,318 | 1/1984 | Connelly, Jr. ............ 433/14 |
| 4,536,154 | 8/1985 | Garton, Jr. et al. ........ 433/8 |
| 4,838,787 | 6/1989 | Lerner ....................... 433/14 |
| 4,936,773 | 6/1990 | Kawaguchi ................ 433/9 |
| 5,011,403 | 4/1991 | Sadoun et al. .............. 433/8 |
| 5,037,297 | 8/1991 | Lerner ....................... 433/14 |
| 5,123,838 | 6/1992 | Cannon ..................... 433/14 |
| 5,127,828 | 7/1992 | Suyama ...................... 433/8 |

Primary Examiner—Gene Mancene
Assistant Examiner—Cindy A. Cherichetti
Attorney, Agent, or Firm—Cushman, Darby & Cushman

[57] ABSTRACT

An orthodontic appliance includes a bracket having a front face provided with a rectangular recess for receiving an archwire and rear face for attachment to a tooth or backing plate with an intermediate segment defining a peripheral groove having a pair of base surfaces which are curved about a common axis for receiving supplemental or primary archwires; the body is provided with a rear segment including a through channel for receiving a retaining pin which has a head for cooperation with a notch formed in the front face; the recess of the front face is angled in two directions to increase the variability of the forces that can be applied to the subjacent tooth in practice.

3 Claims, 3 Drawing Sheets

ORTHODONTIC APPLIANCE

FIELD OF THE INVENTION

The present invention relates to orthodontic appliances and, more particularly to an orthodontic bracket that uses both the advantageous features of the straight wire, edgewise and lightwire correction techniques either singly or in combination to greatly expand the adaptability of the individual brackets of the present invention to move a patient's teeth.

BACKGROUND OF THE INVENTION

The prior art has provided a great variety of different bracket structures for attachment to a tooth with the brackets having structure for accommodating torque imparting wires of various shapes as well as other appliances to apply torque or appropriate force to a tooth to reposition the tooth to improve appearance, bite or to repair damage resulting from accident. In current orthodontic appliances, these brackets may be attached to the teeth directly by means of acid etched bonded adhesives with the forces imparted resulting from the use of metal archwires of various dimensions, alloys and designs. To accommodate the widest variety of different orthodontic problems, the brackets of the prior art have an enormous range of design configurations believed necessary to enable a practitioner to impart specific treatment effects to a patient.

In current orthodontic practice, four types of appliances are in common usage. Of these, the most common include the edgewise appliance, the Begg appliance, the straight wire appliance, and the combination appliance. The introduction of these appliances commenced early this century and continues up to the present day. Of these, the most frequently used are the standard edgewise bracket or the straight wire type of bracket. The acceptance of these two alternatives is due primarily to the ability to simplify control of the tooth in three dimensions. The success of the edgewise or straight wire type of appliance also is believed due to the ability of the archwire slot to automatically produce movements facio-lingually, mesiodistally and axially without special bends in the archwire. This particular appliance is well known for its translatory type of movement and its precision and control.

The Begg type of appliance, such as represented by U.S. Pat. Nos. 3,128,553 of Apr. 14, 1964 and 3,163,933 of Jan. 5, 1965, are generally understood as imparting simple tipping to the tooth without any three dimensional control of any applied forces. It has been characterized by the use of a narrow bracket of the ribbon type which, in its early design, was opened at the incisal end and, in later designs, at the gingival area of the tooth. A retaining pin was employed to retain the archwire in position when a light archwire was employed. In many cases, auxiliary appliances such as springs and wires were required to correct excessive tipping or torquing of the tooth and to coordinate the crown and root position of the teeth.

The combination bracket involves an attempt to combine the edgewise and Begg type of brackets into one structure. With several modifications to accommodate different types of wires or combination of wires, the combination bracket permitted the use of translatory movements in a facial edgewise slot and tipping in either the gingival or incisal Begg slot.

Straight wire orthodontic appliances have been widely accepted in addition to the edgewise techniques as they have been associated with simplified mechanics, arch formation and more precision in finishing procedures. Unfortunately, a number of inherent problems have arisen which have adversely affected their treatment effectiveness. To a large extent, the imparting of a directional force or vector to a tooth depends on the shape and positioning of a rectangular slot in the bracket which receives a complimentary shaped wire. For the manufacturer and the practitioner, however, the requirement of maintaining a large inventory of differently angulated rectangular slots has proven undesirable in view of the expense involved and the difficulty of properly installing such highly selectively employed brackets in patients. As a consequence, manufacturers have endeavored to manufacture a bracket capable of producing regular three dimensional tooth movement but structured so as to accommodate an average tooth anatomy.

Unfortunately, due to the high variability of human tooth anatomy, such brackets have not met with widespread acceptance thus forcing manufacturers to produce several different types of brackets for specific tooth anomalies. This has resulted in the necessity for a practitioner maintaining a wide variety of different brackets in his inventory thereby increasing his costs and that of the patient.

Another difficulty constraining the designers of brackets in this field is the requirement of securing the archwire to the bracket in an effective and safe manner that is comfortable for the patient. In some designs, a compromise has been reached between ease of attachment of the archwire to the bracket and the effectiveness of the bracket in treating the tooth abnormality of the patient.

Additionally, edgewise and straight wire brackets are designed so teeth cannot freely move by tipping. The restriction on tipping movement slows the movement, increases treatment time, increases the forces required and frequently causes an increase in pain and discomfort for the patient. A bracket designed to permit tipping overcomes these disadvantages.

SUMMARY OF THE INVENTION

The present invention provides a bracket structure which effectively confronts each of the foregoing problems and yet provides a bracket which can address a greater range of tooth abnormalities thereby reducing the inventory required by a practitioner as well as the range of specially designed brackets that are usually required in a practice. In one embodiment, the present invention provides a bracket that will retain the benefits of the combination brackets as well as the straight wire bracket technique. Specifically, the bracket of the present invention includes a base on the rear face thereof and a front face which between them define two ribbon or straight wire receiving recesses. The front face is formed with a rectangular recess set at a specific angle relative to the longitudinal axis of the bracket to receive a square archwire similar to the straight wire techniques. A vertical slot is provided adjacent the rear face to receive and hold a fastening device such as a retaining pin which may be employed to assist in securing an archwire or, if needed, a tie wire. In an alternative, the vertical slot can be used without a fastening device to receive a tie wire to retain either a ribbon wire, straight wire or an edgewise archwire in their respective slots or recesses on the bracket.

BRIEF DESCRIPTION OF THE DRAWINGS

A further explanation of the present invention will be given below with reference to the accompanying drawings which disclose a preferred embodiment and in which.

DETAILED DESCRIPTION OF THE INVENTION

Figure 2:
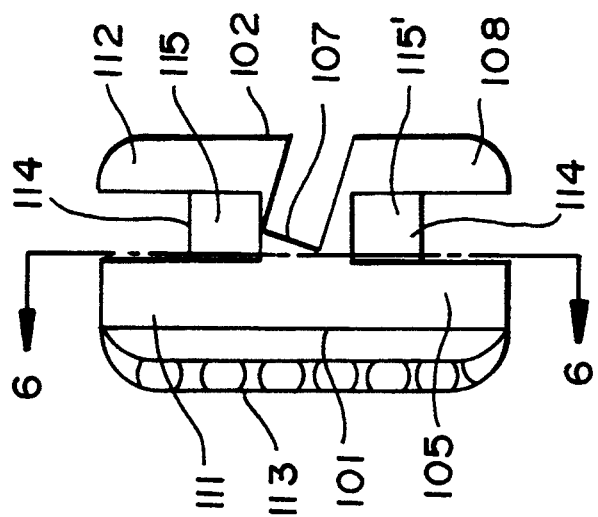
FIG. 2 is a view from one side in elevation of the bracket of FIG. 1.
Figure 1:
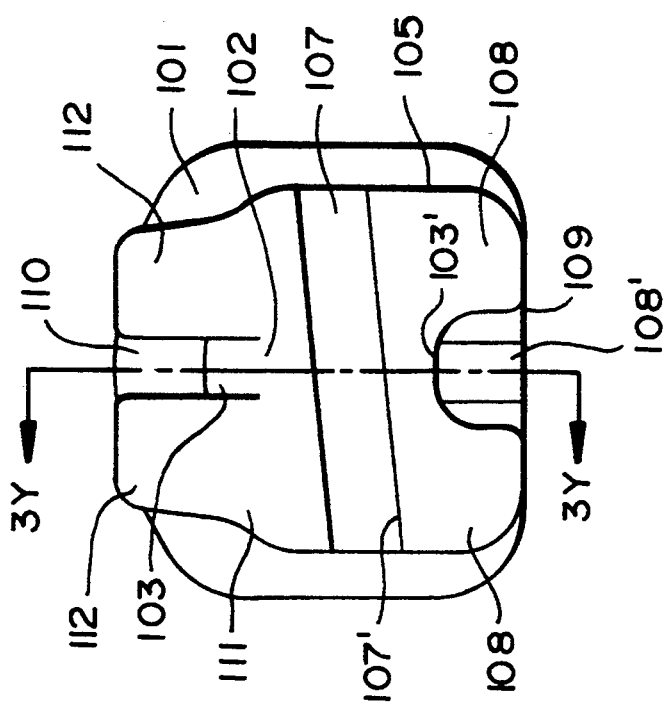
FIG. 1 is a front elevational view of the bracket of the present invention.

Referring now to the drawings wherein like numerals designate corresponding parts throughout the several views, there is shown in FIGS. 1 and 2 front and side views, respectively, of the bracket 101 of the present invention which comprises a front face 111 on a first segment of the body bracket 101 and a second segment carrying the rear face 113 which is adapted to be attached directly to the surface of a patient's tooth or to a base plate or pad which is adhesively secured to the patient's tooth. The front face 111 is formed to have spaced apart upper shoulders 112 separated by a notch 110 having a sloping base 103. The lower shoulders 108 are similarly spaced apart to define an opening 108'. As discussed below, these provide projections which serve several purposes such as providing a post to which a tieing member is applied.

The first segment is spaced from the rear segment carrying the rear face 113 by a distance selected to provide oppositely opening recesses 114 at least one of which has a smoothly curving base surface 115 which is symmetrical about a central axis passing through the bracket 101. The recesses 114 may each be formed with a curved base surface 115 as shown more clearly in FIG. 6.

The front face 111 is formed with a rectangular recess 107 which extends across the width of the front face 111 at an angle to the longitudinal axis of the bracket 101. In addition, as shown in FIG. 2, the inner or base surface 116 of the recess 107 is flat and lies in a plane which also intersects the longitudinal axis of the bracket 101 at an angle so that the recess 107 will extend at an angle to a plane passing perpendicularly through the front and rear faces of the bracket 101 as shown more clearly in FIG. 2.

Figure 3:
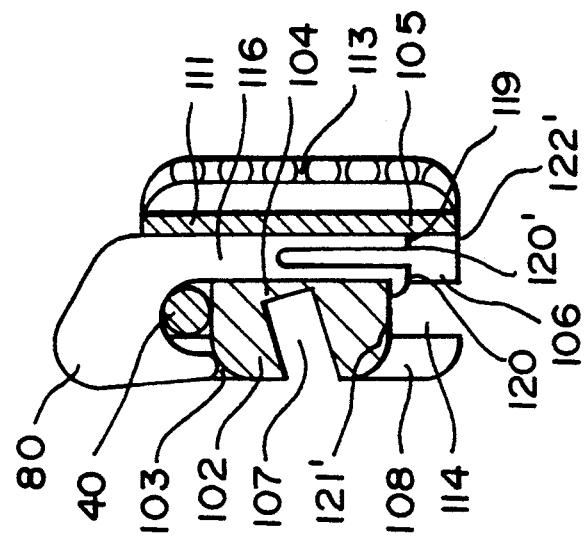
FIG. 3 is a view along lines 3—3 of FIG. 1, but with a fastening device such as a tie pin inserted.
Figure 4:
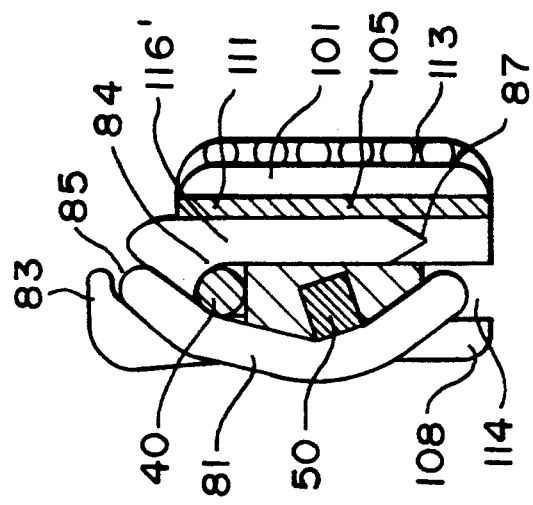
FIG. 4 is a view similar to FIG. 3 but with two archwires held with a combination of a fastening device and tie wire.
Figure 5:
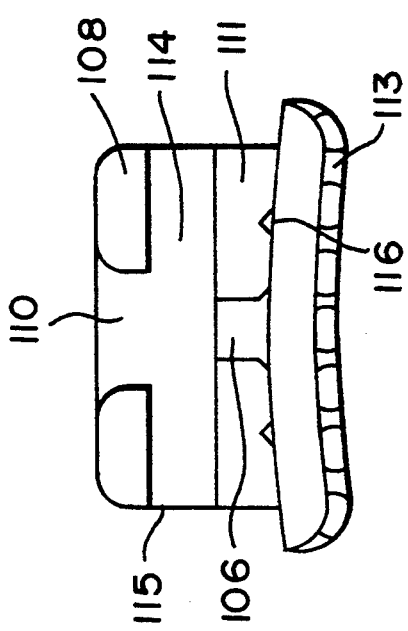
FIG. 5 is a top plan view.

With reference to FIG. 5, it will be seen that a channel 106 is provided in the first segment 111 which extends completely through the bracket 101 as shown in FIGS. 3 and 4.

Figure 6:
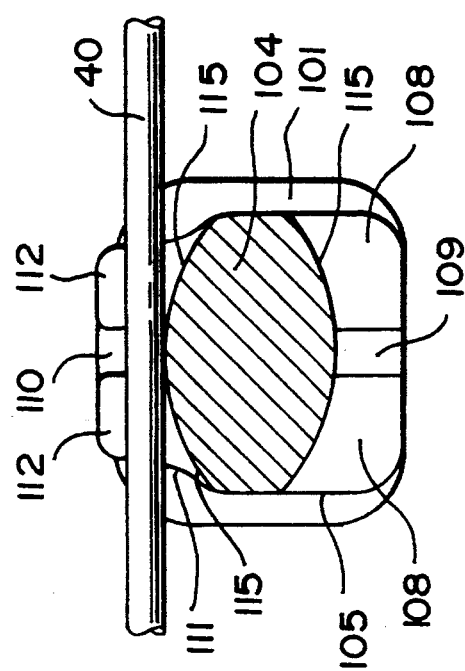
FIG. 6 is a sectional view taken along lines 6—6 of FIG. 2.

As shown in FIG. 6, the curvature of the surfaces 115 is generally symmetrical about a central axis A of the bracket 101. With this configuration, the straight or arch wire 40 when inserted into the upper recess 114 will have a virtual point contact with the surface 115 thus permitting the practitioner significant tipping capability and much greater latitude in adjusting the relative orientations between the wire 40 and the bracket 101 than would be the case where the surface 115 were flat. The incisal surface 115' need not be curved as is shown but it has generally proven to be advisable to adopt this curved configuration to facilitate manufacturing as well as to provide greater tipping capability with the archwire in this recess 114.

Also, as shown in FIG. 5, the rear face 113 may be accurately formed in both the vertical and horizontal direction to accommodate the natural curvature of the majority of teeth of patients.

Figure 7:
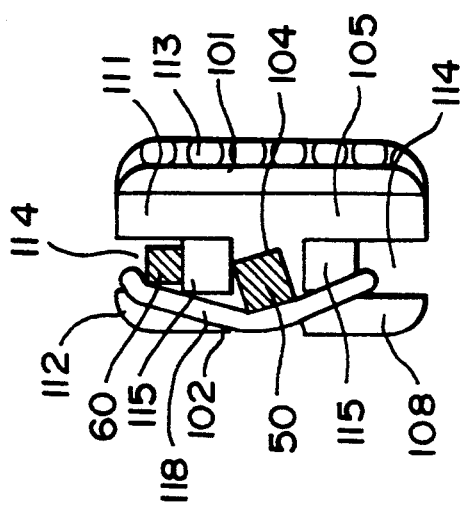
FIG. 7 is a view similar to FIG. 3 but with the archwires held in position by a retaining ligature wire.

As shown in FIG. 7, archwires 50 and 60 are inserted in the respective slots 107 and 114 and held in place in a conventional manner such as by an elastic tie member 118. As is conventional in orthodontics, the tension on the respective wires 50 and 60 can be adjusted to regulate the force imparted to the underlying tooth on which the bracket is mounted. The present invention provides great flexibility and ease in attachment of the tie wire or band 118 due to the provision of the relatively wide, oppositely opening recesses 114 in the structure of the bracket of the present invention.

In FIG. 3, there is shown the bracket 101 of the present invention employed with a single fastening device in the form of a pin 80 having a base 119 which is U-shaped in format to provide a separate leg 120. The leg 120 is provided with an exterior flange to grip the underside of the groove 109 provided in the front face 111 of the bracket 101. The pin 80 is preferably held in place by spring action between the legs 120, 120' when inserted into the channel 106. By providing the lower edge 121' recessed from the lower edge 122' of the bracket, the lower end of the pin 80 will not project beyond the lower edge 122' in use. The head 80 is provided with a downwardly curved opening to retain the wire 40 in one of the recesses 114 against the base surface 115.

In the modification of FIG. 4, the retaining pin 116' is provided with an upwardly opening notch 85 and with a solid column 87 which is received in the channel 106. In this embodiment, the pin 116' is held in position by a retaining wire or band 81 which is preferably an elastic member passing through the opening 85 and underneath and into the lower recess 114 to thereby hold the two wires 40 and 50 in their respective recesses.

Figure 9:
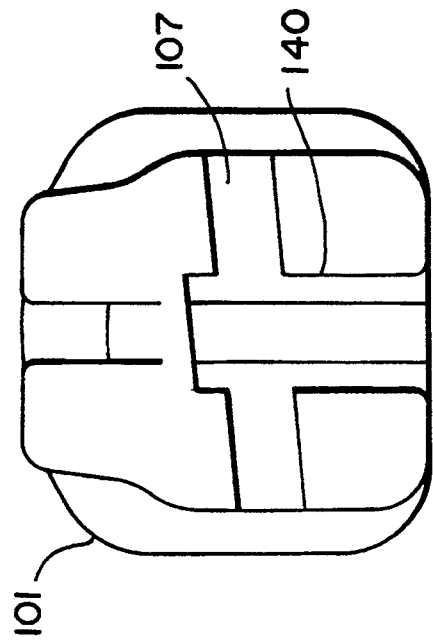
FIG. 9 is a view similar to FIG. 1 but of another alternate embodiment.
Figure 8:
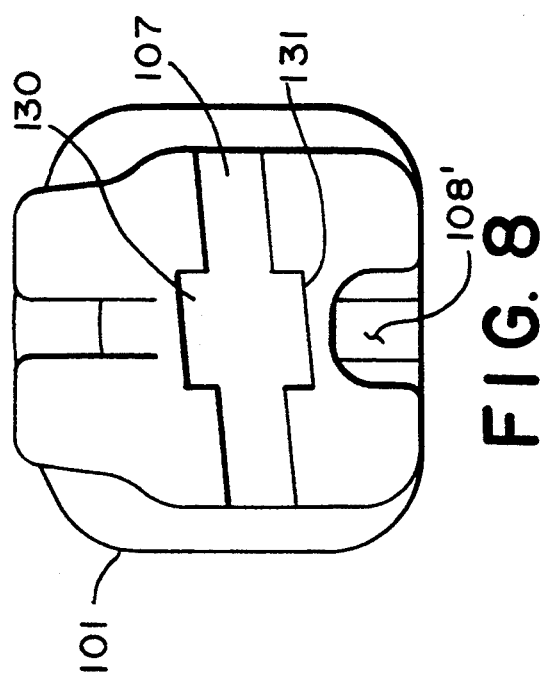
FIG. 8 is a front view in elevation similar to FIG. 1 of an alternate embodiment.

With reference to FIG. 8, a modification of the embodiment of FIG. 1 is shown in front elevation where the recess 107 is provided intermediate its ends with enlarged portions 130 and 131 to reduce surface area and frictional rubbing in the bracket. This construction affords much greater flexibility and force transfer to the tooth than the previous embodiments. In the embodiment of FIG. 9, the lower wall of the recess 131 is eliminated and the front face is provided with a channel opening 140 to facilitate insertion and positioning of the retaining ligature or elastic band.

Having described the invention, it will be apparent to those skilled in this art that various modifications may be made thereto without departing from the spirit and scope of this invention as defined in the appended claims.

What is claimed is:

1. An orthodontic bracket for use with at least one archwire comprising:

a body having a first segment including a rear face for attachment to a tooth surface or a backing plate and a second segment including a front face and an intermediate segment disposed between and spacing said first and second segments apart, said intermediate segment having a peripheral dimension less than the peripheral dimensions of said first and second segments to thereby define a pair of grooves between said first and second segments with each having an inner base surface, at least one of said base surfaces being convexly curved, said first segment having a channel therein for receiving a fastening device, said channel extending generally transversely relative to said base surface of a said groove, a retaining device for holding a wire engaged with said bracket, said retaining device having a first enlarged end and an opposite end having split legs for insertion into said channel of said bracket, said enlarged end having a recess for at least partially surrounding a wire disposed in said groove of said bracket.

2. The invention as claimed in claim 1 wherein one of said legs has a flange protruding outwardly therefrom, said channel through said bracket having a recessed edge engageable by said flange when said retaining device is inserted in said channel.

3. An orthodontic bracket for use with at least one arch wire comprising:

a body having a first segment including a rear face for attachment to a tooth surface or a backing plate and a second segment including a front face and an intermediate segment disposed between and spacing said first and second segments apart, said intermediate segment having a peripheral dimension less than the peripheral dimensions of said first and second segments to thereby define a pair of grooves between said first and second segments with each having an inner base surface, at least one of said base surfaces being convexly curved, said first segment having a channel therein for receiving a fastening device, said channel extending generally transversely relative to said base surface of a said groove, said bracket including a retaining device for holding a wire engaged with said bracket; said retaining device having a first enlarged end and an opposite end having split legs for insertion into said channel of said bracket, said enlarged end having a recess for at least partially surrounding a wire disposed in a said groove of said bracket, one of said legs having a flange protruding outwardly therefrom, said channel through said bracket having a recessed edge engageable by said flange when said retaining device is inserted in said channel, said channel having a selected length and said pin has a length less than said selected length.

* * * * *